United States Patent [19]

Moody et al.

[11] 4,152,098

[45] May 1, 1979

[54] MICROPUMP

[76] Inventors: Norman F. Moody, 44 Coldstream Ave., Toronto; Ivan P. Clark, 7152 Ridgeland Cres., Mississauga, both of Canada

[21] Appl. No.: 756,579

[22] Filed: Jan. 3, 1977

[51] Int. Cl.$^2$ ............................................. F04B 43/04
[52] U.S. Cl. .................................. 417/413; 128/213 R; 128/214 F; 128/260; 417/417
[58] Field of Search ..................... 417/413, 417, 415; 128/214 F, 213, 260

[56] References Cited

U.S. PATENT DOCUMENTS

| 2,809,589 | 10/1957 | Randolph | 417/413 |
| 3,134,125 | 5/1964 | Kaiser | 417/413 |
| 3,174,433 | 3/1965 | Roosa | 417/413 |
| 3,496,872 | 2/1970 | Riester et al. | 417/413 |
| 3,527,220 | 9/1970 | Summers | 128/260 |
| 3,951,147 | 4/1976 | Tucker et al. | 128/214 F |
| 4,013,074 | 3/1977 | Siposs | 128/214 F |

Primary Examiner—C. J. Husar

[57] ABSTRACT

A micropump capable of delivering very small, predetermined quantities of liquid, e.g. 0.1–100 microliters per stroke, is provided. The pump has a flexible, resilient diaphragm which operates as a movable resilient wall of a pumping chamber, under electromagnetic actuation of a plunger, to cause the pumping action. Other locations of the same resilient diaphragm, in co-operation with curved surfaces on the body structure, act as valves for the inlet and outlet conduits of the pump. The overall size of the pump need be no greater than about 4 cubic cm. Many of the liquid flow conduits therein are formed by co-operating channels or grooves cut in individual co-operating parts of the pump body. The pump may be surgically implanted into a patient's body, to deliver to the desired body location a very small, measured amount of pharmaceutical from an internal or external reservoir thereof, as and when desired.

12 Claims, 4 Drawing Figures

MICROPUMP

FIELD OF THE INVENTION

This invention relates to pumps, more especially to a micropump adapted to deliver very small quantities, e.g. as low as 0.1 microliters, of liquid per stroke. Such a pump is useful in pharmaceutical dispensing and packaging, chemical analysers, isotope dispensing and the like.

BACKGROUND OF THE INVENTION

There is a need for a satisfactory pump which can be economically manufactured and which is capable of delivering quantities of liquid in the microliter range, to an accurate degree, as and when required. One area where such a need is felt is in medical applications, where accurate but very small doses of pharmaceuticals have to be delivered to a patient according to a regular or irregular timetable. A specific example is in the supply to a patient of an anticoagulant preparation in the treatment of thrombosis, or the supply to a patient of an insulin preparation in the treatment of diabetes. These quantities can be as small as 0.1 microliters. The design and manufacture of a micropump which can accurately deliver such a small but predetermined amount of liquid per stroke presents considerable difficulty.

Increasing attention is now being paid to the possibility of administering pharmaceuticals to patients from reservoirs of pharmaceuticals which have been physically implanted into the body. The pharmaceuticals can then be released close to the specific body region where their action is required, instead of being administered orally. They can be released from implants as and when the patient feels the need of medication, or according to a prearranged timetable or program, e.g. by external means operated externally of the body. The operation of such implant medications systems would be enhanced in some cases by the inclusion in the system of an implantable micropump, capable of delivering very small quantities of liquid per stroke and operable by means controlled from an implanted mechanism or from outside the body.

BRIEF DESCRIPTION OF THE PRIOR ART

Pumps of the standard, sliding piston type, theoretically capable of delivering 0.1 mls. or more of liquid per stroke, are known and available. These, however, are not capable of delivering the very minute, but controlled, liquid quantities commonly needed in pharmaceutical work.

It is also known to implant into a patient's body a source or reservoir of pharmaceutical, which can be released from the reservoir by application of external means as and when required. However, we are aware of no previous proposal for an implantable micropump capable of delivering from a drug reservoir, a minute but measured quantity of liquid, operated by external means, as and when required.

BRIEF SUMMARY OF THE INVENTION

It is an object of the present invention to provide a micropump capable of delivering predetermined quantities of liquid of as little as 0.1 microliters per stroke.

It is a further object of the present invention to provide a micropump of the above type which is relatively simple and economic to manufacture.

It is a further object of the present invention to provide a micropump of the above type which can if desired be implanted in a patient's body, and operated by means controllable internally or externally of the patient's body.

Other objects and advantages of the invention will be apparent from the following description.

In summary, the present invention provides a pump for dispensing predetermined small quantities of liquid material, said pump comprising:
  a body structure;
  an inlet conduit in the body structure adapted to be connected to a source of liquid to be pumped;
  an inlet valve in the body structure;
  a pump chamber in the body structure, in fluid communication with said inlet conduit via said inlet valve;
  an outlet valve in the body structure;
  an outlet conduit in the body structure in fluid communication with said pump chamber via said outlet valve;
  a pumping member defining a boundary of the pump chamber, said pumping member comprising a flexible, resilient, substantially liquid impermeable diaphragm movable relative to the pump chamber between a first, enlarged pump chamber defining position and second, restricted pump chamber defining position;
  operating means associated with the pumping member and adapted to move the pumping member between its first position and its second position.

The pump of the present invention is capable of delivering predetermined quantities of liquid in the range 0.1–100 microliters per stroke. The delivery rate can be up to 20 strokes per second. The body structure of the pump can be arranged to enclose all of the moving parts, and can itself be made of biocompatible and biostable material, such as thermoplastic polycarbonate, so that it can if desired be implanted into a patient's body.

DESCRIPTION OF THE PREFERRED EMBODIMENT

In the preferred embodiment of the invention, the pumping member is a resilient diaphragm of a liquid impermeable, inert material, chosen with regard to its stability and inertness to the material which is being pumped. It may be of synthetic rubbery polymeric material, or of metal. Especially preferred is segmented polyurethane, but other suitable materials will be apparent. The diaphragm forms a flexible wall of the pumping chamber, and is flexed into the pumping chamber to increase the pressure of liquid therein by an electromagnetically operated actuating plunger bearing on the side of the diaphragm remote from the pumping chamber. When the actuating plunger is withdrawn, the resilience of the diaphragm causes it to return to enlarge the pumping chamber and thereby decrease the pressure on the liquid therein. The diaphragm is suitably clamped in a stressed condition around the periphery of the pumping chamber boundary which it forms.

Preferably also, both the inlet valve and the outlet valve are constituted by apertured portions of the same diaphragm, these valve portions thereof being remote from the pump chamber forming portion of the diaphragm, and co-operating with curved surfaces on the pump body over which the diaphragm is stretched. The inlet and outlet conduits terminate at the respective curved surfaces, at a location thereon remote from the position of registry of the apertures in the diaphragm with the curved surface. By this means, the respective apertured diaphragm portions may be urged against the curved surfaces to close the respective valves, by pressure exerted on the liquid in the pumping chamber or away therefrom, so as to open the valves and allow communication between the pump chamber and the respective inlet and outlet conduit. The degree of curvature of the curved surfaces forming parts of the inlet and outlet valves control the pressures at which the valves will open and close, since this determines the tension with which the diaphragm is stretched over the curved surfaces and hence the pressures required to lift the diaphragm and open the valves. This degree of curvature can be preselected on manufacturing the pump, so as to arrange for a pump properly designed to operate under specific conditions and with specific associated driving means, etc. As the curvature of these valve surfaces decreases, the forward pressure at which they open approaches zero. It is important to know the source pressure which will cause breakthrough of the whole pump this being set by the curvatures of these valve surfaces, and thus to be able to control the source pressure accordingly.

In the preferred arrangement, the body structure of the pump is conveniently made of a main body having said inlet conduit and said outlet conduit drilled therethrough, a valve plate secured to the bottom surface of the main body, the diaphragm being clamped between the main body and the valve plate, and a cover plate secured to the surface of the valve plate remote from the main body. The pump chamber and the communication between the pump chamber and the inlet valve and the outlet valve may thus be formed by co-operating grooves cut in at least one of the adjacent surfaces of the valve plate and the cover plate. This is a particularly convenient method of fabricating the pump according to the invention, since detailed machining and drilling and the like of conduits is to be avoided as far as possible, on items of this small size. The curved surfaces on the pump body are thus conveniently made on the co-operating surfaces of either or both of the pump body and the valve plate.

Thus, the preferred embodiment of the present invention has a pump body consisting of a small number of injection molded, thermoplastic pressings, and a single flexible diaphragm which satisfies the needs of both pumping element and the two non-return valves. The respective parts are best secured together by means of adhesives. In this manner, a simple and economic micropump is manufactured and assembled. In fact, the pump can be so economically manufactured that it can be treated largely as a disposable item, where cleaning or sterilization is uneconomic, in various medical applications. Various thermoplastics can be employed in the manufacture of the body components, and a variety of flexible diaphragm materials can be employed as the pumping element.

With the pump according to the preferred embodiment of the present invention the precision work necessary to make the necessary conduits, channels, curved surfaces and the like is predominantly achieved in the making of a suitable mold for the respective thermoplastic parts. Once this has been achieved, the manufacture and assembly of large quantities of pumps according to the present invention requires only unskilled labour to perform, and is a rapid and economic undertaking.

BRIEF REFERENCE TO THE DRAWINGS

In the drawings, like reference numerals indicate like parts.

DETAILED DESCRIPTION OF THE SPECIFIC PREFERRED EMBODIMENT

Figure 1:
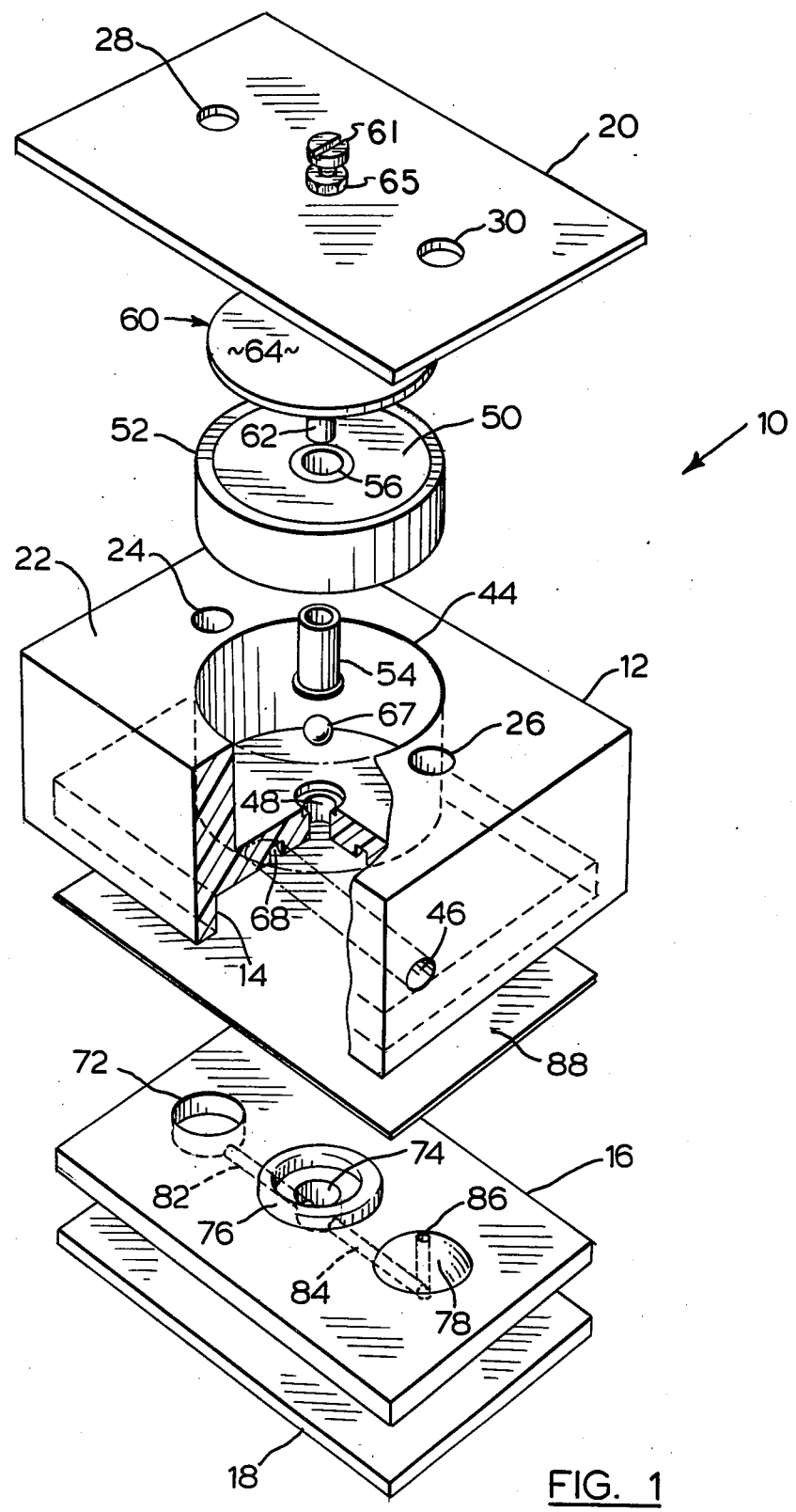
FIG. 1 is an exploded perspective view of a micropump according to a specific preferred embodiment of the invention.

The pump 10 according to the invention has a body structure consisting essentially of a main body 12 of rectangular box-like overall shape. A rectangular recess 14 is located in the bottom face of the main body 12, the recess 14 extending to within a short distance of the sides of the main body 12. A rectangular valve plate 16 is provided, of substantially the same surface shape and size as the recess 14 on the bottom surface of the main body 12, and adapted to be a snug fit therein on assembly of the pump 10. The thickness of the valve plate 16 is less than the depth of the recess 14. A rectangular cover plate 18 is also provided having substantially the same dimensions as the valve plate 16, and adapted to fit over the bottom surface of valve plate 14 and in the lower part of recess 14 in the main body 12, when the pump is assembled. There is also provided a rectangular top cover plate 20, adapted to fit over the top rectangular surface 22 of the main body 12 when the pump is assembled.

Figure 2:
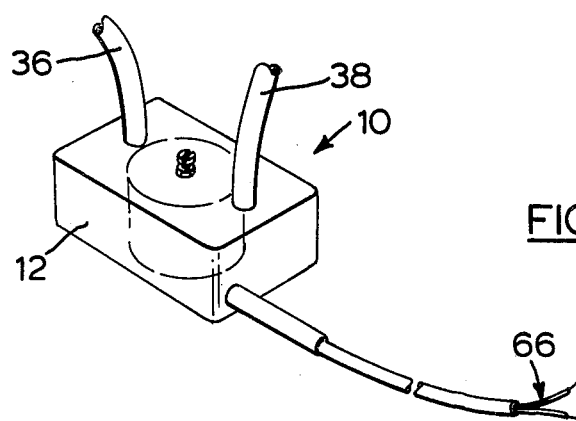
FIG. 2 is a perspective view of the assembled pump of FIG. 1.
Figure 3:
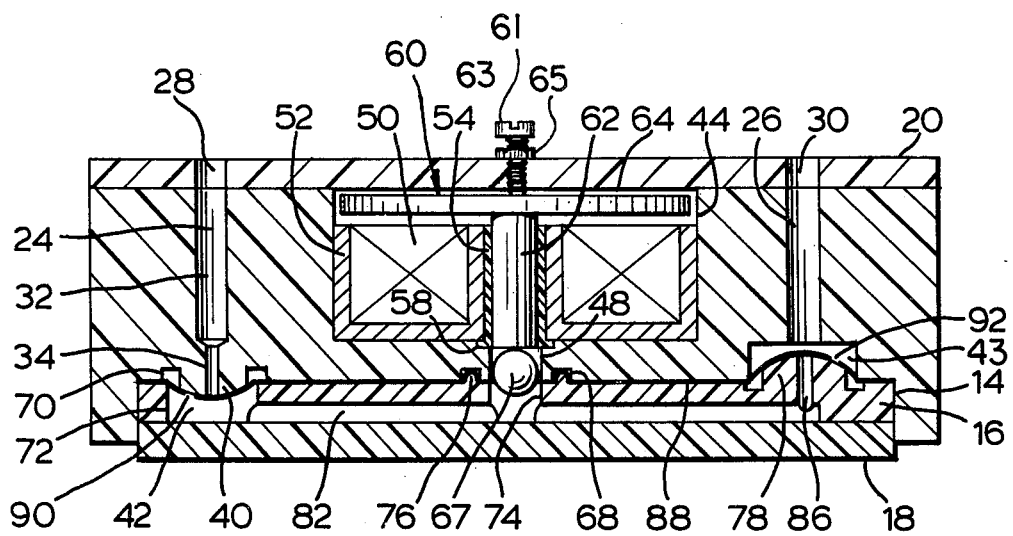
FIG. 3 is a vertical longitudinal cross section through the center of the assembled pump.
Figure 4:
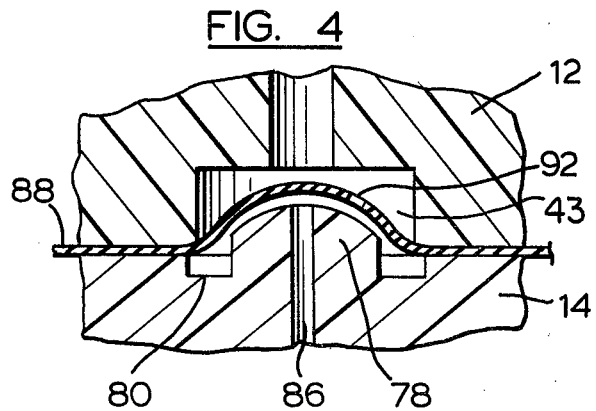
FIG. 4 is a cross section, similar to FIG. 3, of a detail of a valve of the pump of FIG. 3, in an open position.

Extending downwardly through the main body 12, on each side of the center and on the longitudinal center line thereof, is a drilled cylindrical aperture. The first such aperture 24 forms an inlet conduit 24 and the second such aperture forms an outlet conduit 26. Respective apertures 28, 30 are provided in the top cover plate 20, to register with the inlet conduit 24 and outlet conduit 26 in the assembled pump. The inlet conduit 24 in the main body 12 has an enlarged portion 32 at its upper part and a narrow portion 34 at its lower part, whilst the outlet conduit 26 is of substantially the same diameter as enlarged portion 32 throughout its length. In the assembled pump, as shown in FIG. 2, an inlet tube 36 and an outlet tube 38 are received respectively in the inlet conduit 24 and the outlet conduit 26, as snug fits in the upper portion of these conduits, the inlet tube 36 extending down in conduit 24 as far as the end of the enlarged portion 32 thereof. The narrow portion 34 of the inlet conduit 24 terminates substantially at the center of a generally part spherical protrusion 40 extending from the bottom surface of the main body 12 and within the recess 14, the inlet conduit extending through the bottom surface of the main body 12, as best seen in FIG. 3. A cylindrical recess 42 is formed between main body 12 and cover plate 18, below protrusion 40. The lower end of outlet conduit 26 extends into a cylindrical recess 43 extending upwardly in the bottom surface of the main body 12, within the rectangular recess 14, as best seen in FIG. 3 and FIG. 4.

The center of the main body 12, between the inlet and outlet conduits, is provided with a relatively large blind aperture 44, of circular cross section, extending to the top surface of the main body 12. A laterally extending passageway 46 is bored through main body 12 from the bottom of aperture 44 through a side wall thereof to allow access from outside the body to aperture 44, for the passage of electrical power leads therethrough as described below. A small generally cylindrical aperture 48 extends from the centre of the bottom extremity of aperture 44, through the bottom of the main body 12. In the assembled pump 10, an electromagnetic coil arrangement 50 of annular configuration and having a ferrite core 52 therearound is disposed as a snug fit in the large blind aperture 44. An anti-friction sleeve 54 of polytetrafluoroethylene is located in the center aperture 56 of the annular coil arrangement 50, the sleeve 54 having a lower outer annular flange 58 received under the ferrite core 52 in a complementary stepped formation on the bottom surface of the main body 12, in the assembled pump, so as to retain the sleeve 54 therein.

An armature or plunger 60, of magnetic steel, having a downwardly extending cylindrical shaft 62 and an upper circular disc 64 is provided, the shaft 62 being slidably received in the sleeve 54 and the disc 64 being disposed in the top of large blind aperture 44 and being movable with respect to the main body 12. A set screw 61 extends threadably through a screw threaded aperture 63 in the top cover plate 20, the bottom end of set screw 61 engaging against the top of disc 64 of the plunger 60 so as adjustably to limit the upward travel and hence the stroke of plunger 60. A locking nut 65 is provided on set screw 61, to bear against the top surface of cover plate 20 and lock set screw 61 in predetermined position. Power leads 66 (FIG. 2) are connected to the electromagnetic coil arrangement 50, and extend through the lateral passageway 46 through the main body 12, to a suitable power source. The plunger 60 is movable up and down with respect to the main body 12, on energizing the coil arrangement 50. In the small aperture 48 through the bottom of main body 12 is provided a ball 67 freely slidable with respect to the main body 12, and contacting but not secured to the bottom end of shaft 62 of plunger 60.

The bottom surface of the main body 12, in the recess 14, is provided at its center with an annular groove 68 surrounding the small center aperture 48. The bottom surface of the main body 12 is provided also with an annular groove 70 surrounding the part spherical protrusion 40.

The valve plate 16 has, near one end thereof, a circular aperture 72 therethrough, of substantially the same diameter as that of the part spherical protrusion 40 on the bottom surface of the main body 12. The aperture 72 is adapted to register with part spherical protrusion 40 when the main body 12 and the valve plate 16 are assembled. A central circular aperture 74 is provided at the center of the valve plate 16, of substantially the same diameter as that of the small center aperture 48 extending through the bottom of the main body 12, and registering therewith when the pump is assembled. An annular lip 76 on the valve plate 16 surrounds this central aperture 74, and registers with the annular groove 68 on the lower surface of the main body 12 in the assembled pump. The end of the valve plate remote from the circular aperture 72 is provided, substantially on its center line, with a part spherical protrusion 78 extending towards the main body 12 and registering with the cylindrical recess 42 in the main body 12 in the assembled pump. The protrusion 78 is surrounded by an annular groove 80 in the valve plate 16.

On its lower surface, which in the assembled pump 10 is disposed away from the main body 12, the valve plate 16 is provided with 2 longitudinally extending central grooves, the first 82 of which extends from the circular aperture 72 in the valve plate 16 to the central aperture 74 therein, and the second 84 of which extends from the central aperture 74 in the valve plate 16 to the part spherical protrusion 78 thereon. A vertically extending conduit 86 extends from the end of second groove 84 up through the part spherical protrusion 78, in registry with outlet conduit 26 in the main body 12, in the assembled pump 10.

A pumping member in the form of a generally rectangular resilient diaphragm 88 of segmented polyurethane is provided, the diaphragm 88 being located between the upper surface of the valve plate 16 and the lower surface of the main body 12, in the recess 14, and clamped therebetween in the assembled pump 10. The diaphragm is of a size to fit snugly in the recess 14, i.e. a size generally corresponding to the size of valve plate 16, as viewed in plan. The diaphragm 88 extends over the respective part spherical protrusions 40 in the main body 12 and 78 in the valve plate 16. A first small aperture 90 is provided in the diaphragm 88 at a location where it passes under part spherical protrusion 40 on the main body 12, the aperture 90 being out of registry with the lower end 34 of inlet conduit 24. A second small aperture 92 is similarly provided at the other end of the diaphragm 88, where it overlies part spherical protrusion 78, but out of registry with conduit 86. It will be appreciated that, in its normal condition, the diaphragm 88 is a flat rectangular resilient sheet, so that in the assembled pump it is stretched around the surface of the part spherical protrusions 40, 78 and also prestressed by the central annular lip 76 on the valve plate 16.

The pump assembly is completed by a cover plate 18, which is a flat rectangular plate and fits within recess 14 in the bottom of the main body 12. In the assembled pump, it closes off the end circular aperture 72 through the valve plate 16, and the central circular aperture 74 therein, to form chambers therewith in the interior of the pump 10. It also closes off the bottom of grooves 82 and 84 of the valve plate, so that these form passageways in the interior of the assembled pump, respectively communicating between the central aperture 74 and the vertically extending conduit 86.

The means for assembly of the pump will be readily apparent from the foregoing description and the drawings. The top cover plate 20, the main body 12, the valve plate 16 and the cover plate 18 are made as one piece pressings or stampings of suitable thermoplastic material, for example a clear thermoplastic polycarbonate. The laterally extending passageway 46, the inlet conduit 24 and the outlet conduit 26 in the main body 12, and the vertically extending conduit 86 in the valve plate 16, are drilled therein after fabrication. A small amount of lubricant is applied to the ball 67 before this is assembled in the pump. The diaphragm 88 is adhesively secured to both the bottom surface of the main body portion 12 and the top surface of the valve plate 16, so that it extends around the part spherical protrusions 40, 78, and over the lip 76, extending into the groove 68. The diaphragm 88, in combination with the part spherical protrusions 40, 78, forms valves for the pump in operation, so that the diaphragm must not be struck down at these locations. The annular groove 70 surrounding the protrusion 40 in the bottom surface of the main body part 12, and the annular groove 80 surrounding the part spherical protrusion 78 in the upper surface of valve plate 16, act as reservoirs for excess adhesive which may be applied to the surfaces of the diaphragm 88 on assembly, and prevent the accidental application or running of adhesive to stick down the membrane at the part spherical protrusions. To some extent, a similar function is performed by annular groove 68 surrounding the central aperture, ensuring that adhesive does not reach the middle part of the membrane where it would cause the ball 67 to be adhered thereto. However, the primary function of groove 68 and co-operate lip 76 is to stretch the diaphragm at this central location, to ensure that it is in tension where it is operated on by the ball 67, thereby to ensure proper return of the diaphragm 88 at this location at the end of an operating stroke, due to its resilience.

The top cover plate 20, when adhesively applied to the top surface of the main body part 12, effectively seals the pump body, and retains therein the plunger 60, antifriction sleeve 56 and ball 67, all of which parts are essentially loose, sliding fits with respect to one another and with respect to the main body 12 of the pump. The magnetic coil assembly 50 is glued into position. The top cover plate 20 can form a hermetic seal, to ensure that material to be pumped does not contact the metallic parts used therein, and to ensure that a biocompatible finished structure is obtained, with metal parts totally enclosed and out of contact with the environment which will contact the pump body exterior.

In operation, after assembly of the pumps as shown in FIG. 3, it is first necessary that the inlet conduit 24, chamber-recess 72, passageway 82, central chamber 74, passageway 84, conduit 86 and outlet conduit 26 be filled with liquid, since the pump is not self priming. On a downward stroke of plunger 60, caused by electromagnetic actuation of coil assembly 50, ball 67 pushes diaphragm 88 resiliently downwardly, further into chamber 74, thereby increasing the pressure of liquid in the chambers, below the level of the diaphragm. An inlet valve at the bottom of the inlet conduit 24 is formed by diaphragm 88 stretched across part spherical protrusion 40. In the position shown in FIG. 3, the diaphragm effectively closes and seals the end of inlet conduit 24. Increase of pressure in the liquid inside the pump, caused by the downward stroke of plunger 60, urges the diaphragm 88 more closely into co-operation with the part spherical protrusion 40, and effectively seals off inlet conduit 24.

Diaphragm 88 in co-operation with part spherical protrusion 78, at the other side of the pump, effectively forms an outlet valve. Increase of pressure on the liquid in the pump, caused by the downward stroke of plunger 60, urges diaphragm 88 out of close contact with protrusion 78, to the open valve position shown in FIG. 4, in which liquid may travel up from passageway 84, through vertically extending conduit 86, around the top surface of part spherical protrusion 78, through small aperture 92, and then out through the outlet conduit 26.

At the end of a pumping stroke, when the electromagnetic action of the coil assembly 50 is ceased, the resilience of the diaphragm at the center portion pushes the ball 67 and hence the plunger 60 upwards, until the diaphragm resumes its initial prestressed position, and disc 64 abuts against set screw 61. By so doing, the volume of the pumping chamber inside the body of the pump is increased, and there is reduced pressure on the liquid contained in the various passageways. Such reduction in pressure urges the diaphragm back into close, sealing contact with the upper surface of part spherical protrusion 78, thereby closing the outlet valve, the small aperture 92 in the diaphragm being out of registry with the outlet conduit 86, and being urged against the upper surface of the part spherical protrusion 78 in liquid sealing engagement therewith. Simultaneously, at the other end of the pump, this reduction in pressure urges the respective part of the diaphragm 88 away from close sealing contact with downwardly extending part spherical protrusion 40, so that liquid communication is provided between the inlet conduit 24 and the chamber formed by the circular aperture 72 in the valve plate 16, and thence into the pumping chamber of the pump.

In effect, therefore, the inlet valve and outlet valve are essentially the same, and operate in the same manner, one being the reverse of the other. The amount of liquid which is pumped on each stroke of the pump can be determined by suitable arrangement of the size of the pumping chamber, i.e. the diameter of the central circular recess 74 in the valve plate, and also by the amount of travel of ball 67 on each stroke. This in turn is determined by the length of the stroke of the plunger 60 on electromagnetic actuation. The volume pumped per pumping stroke can be limited either by limiting the travel of plunger 62, by engagement of disc 64 with the top of ferrite core 52 or a packing formation carried thereon, for example, or alternatively by arranging for ball 67 to press diaphragm 88 into engagement with bottom wall of chamber 74, at the end of its downward stroke. The provision of such positive stop means defining the initial position and the pumping position of the diaphragm permits precise control of the volume swept per stroke of the pump. The pump will give one delivery stroke for each application of electric current to the electromagnetic coil assembly 50. The frequency of operation of the pump is thus readily arranged. The pump can be arranged to give anything up to about 20 strokes per second. Strokes can be effected as infrequently as desired.

When the parts are disposed in the initial, nonpumping arrangement, the diaphragm 88 is stressed downwardly from the horizontal position by ball 67, around lip 76 as shown in FIG. 3. This arrangement allows more accurate control of pumping volumes, by ensuring that the diaphragm is always in contact with the ball. If the ball 67 were withdrawn further upwardly, there would be a risk that liquid pressure in the pumping chamber would cause the diaphragm to follow the ball upwardly from its horizontal position and hence render the precise pumping volume per stroke indefinite.

The entire dimensions of the pump according to the specific embodiment can be extremely small. For example, the pump as illustrated may be about 2¼ cm. in overall length, about 1½ cm. in overall width, and about 1.0 cm. in thickness. The pump can be arranged to deliver extremely small quantities of liquid per stroke, down as low as 0.1 microliters. The pump arrangement according to the invention substantialy eliminates back flow, which it is necessary to avoid in a pump which is to handle such microscopic amounts of liquid on each stroke.

In an alternative arrangement to that illustrated, there may be included a set screw protruding through the top wall to engage the top of disc 64, thereby ajustably limiting its stroke and defining its rest position. Such an arrangement allows pumps of various different stroke volumes to be made from the same mold.

In a further embodiment, the electromagnetic core, windings and plunger may be made separable from, and even exteriorly of, the remainder of the pump, so that these relatively expensive parts can be recovered and reused, when the remaining parts are discarded. Normally, such a two-part pump would not be implantable.

The pump according to the present invention shows particular utility in the dispensing of pharmaceuticals. For this reason, it is preferred to make all of the parts which will contact the liquid to be pumped, namely the top cover plate, pump body, valve plate and cover plate, as well as the diaphragm, from inert materials which are not affected by the liquid to be pumped. As noted biocompatible plastics materials are normally used for exterior parts, but metals such as stainless steel can be used if desired.

There are however many other applications for a pump according to the present invention, capable of delivering such small quantities of liquid. For example, if finds utility in the packaging of pharmaceuticals in small quantities, in biochemical analyses where very small quantities of reagents often have to be measured and in the dispensing and packaging of radioactive isotopes, which are often handled in extremely small quantities.

It will be appreciated that the embodiment described and illustrated herein is by way of example only, and is not to be construed as limiting the scope of the invention. Other arrangements can be made within the skill of the art, without departing from the siprit of the invention, the scope being defined only in the appended claims.

We claim:

1. A pump for dispensing predetermined small quantities of liquid material, said pump comprising:
   a body structure;
   an inlet in the body structure adapted to be connected to a source of liquid to be pumped;
   an inlet valve in the body structure;
   a pump chamber in the body structure, in fluid communication with said inlet conduit via said inlet valve;
   an outlet valve in the body structure;
   an outlet conduit in the body structure, in fluid communication with said pump chamber via said outlet valve;
   a pumping member defining a boundary of the pump chamber, said pumping member comprising a flexible, resilient, substantially liquid impermeable diaphragm movable relative to the pump chamber between a first, enlarged pump chamber defining position and a second, restricted pump chamber defining position, the diaphragm having a greater degree of resilient stress when in its second position than when in its first position;
   operating means associated with the resilient pumping diaphragm and movable from an initial position to a diaphragm stressing position to cause discharge of fluid material through the outlet valve upon actuation of said operating means so as to move the diaphragm from its first position to its second position;
   the diaphragm returning to its first position, and causing return of the operating means to its initial position, by resilient relaxation of said diaphragm;
   said return movement of the diaphragm by resilient relaxation causing opening of the inlet valve to permit fluid to enter the pump chamber therethrough.

2. A pump for dispensing predetermined small quantities of liquid material, said pump comprising:
   a body structure;
   an inlet in the body structure adapted to be connected to a source of liquid to be pumped;
   an inlet valve in the body structure;
   a pump chamber in the body structure, in fluid communication with said inlet conduit via said inlet valve;
   an outlet valve in the body structure;
   an outlet conduit in the body structure, in fluid communication with said pump chamber via said outlet valve;
   a pumping member defining a boundary of the pump chamber, said pumping member comprising a flexible, resilient, substantially liquid impermeable diaphragm movable relative to the pump chamber between a first, enlarged pump chmber defining position and a second, restricted pump chamber defining position;
   an operating means comprising a plunger slidable within a cavity in the pump body structure, the plunger being adapted to stress the diaphragm resiliently into the pump chamber to pressurize liquid therein on actuation thereof and cause discharge of liquid material through the outlet valve, the plunger being withdrawable to an initial position on cessation of the actuation, withdrawal of said plunger being accompanied by relaxation of the diaphragm to cause opening of the inlet valve to permit fluid to enter the pump chamber therethrough;
   an adjustable set screw engaging the operating means in its initial position, and adjustable to limit the stroke of the operating means on actuation, said set screw being accessible for adjustment externally of the body structure of the pump.

3. A pump for dispensing predetermined small quantities of liquid material, said pump comprising:
   a body structure;
   an inlet in the body structure adapted to be connected to a source of liquid to be pumped;
   an inlet valve in the body structure;
   a pump chamber in the body structure, in fluid communication with said inlet conduit via said inlet valve;
   an outlet valve in the body structure;
   an outlet conduit in the body structure, in fluid communication with said pump chamber via said outlet valve;
   a pumping member defining a boundary of the pump chamber, said pumping member comprising a flexible, resilient, substantially liquid impermeable diaphragm having a pumping portion which defines the boundary of said pump chamber, and a clamping portion surrounding said pumping portion and clamped between elements of the pump body structure surrounding the pump chamber, said pumping portion being movable relative to the pump chamber between a first, enlarged pump chamber defining position and a second, restricted pump chamber defining position, the diaphragm having a greater degree of resilient stress when in its second position than when in its first position;

operating means acting on the pumping portion of the diaphragm and movable from an initial position to a diaphragm stressing position upon actuation of said operating means so as to move the diaphragm from its first position to its second position, the diaphragm returning to its first position and causing return of the operating means to its initial position by resilient relaxation of said diaphragm;

said outlet valve comprising an apertured flexible resilient substantially liquid impermeable diaphragm and a curved surface on the pump body over which the diaphragm is stretched, the curved surface of the outlet valve being convexly curved in a direction towards the outlet conduit, the outlet conduit terminating at said curved surface at a location thereon remote from the position of registry of the aperture in the diaphragm with the curved surface.

4. The pump of claim 3 wherein the body structure is of biocompatible and biostable material, and encloses and substantially hermetically seals the moving parts of the pump therein.

5. The pump of claim 3 wherein the operating means comprises an electromagnetically operated plunger slidable within a cavity in the pump body structure, the plunger being adapted to stress the diaphragm resiliently into the pump chamber to pressurize liquid therein on electromagnetic actuation thereof, said plunger being withdrawn to its initial position by resilient return of the diaphragm from the pump chamber on cessation of said electromagnetic actuation.

6. The pump of claim 5 wherein the diaphragm in its initial position is prestressed by and in contact with parts associated with said plunger.

7. The pump of claim 6 including positive stop means defining the initial position and the pumping position of said diaphragm.

8. A pump for dispensing predetermined small quantities of liquid material, said pump comprising:
 a body structure;
 an inlet in the body structure adapted to be connected to a source of liquid to be pumped;
 an inlet valve in the body structure;
 a pump chamber in the body structure, in fluid communication with said inlet conduit via said inlet valve;
 an outlet valve in the body structure;
 an outlet conduit in the body structure, in fluid communication with said pump chamber via said outlet valve;
 a pumping member defining a boundary of the pump chamber, said pumping chamber member comprising a flexible, resilient, substantially liquid impermeable diaphragm having a pumping portion which defines the boundary of said pump chamber, said pumping portion being movable relative to the pump chamber between a first, enlarged pump chamber defining position and a second, restricted pump chamber defining position, the diaphragm having a greater degree of resilient stress when in its second position than when in its first position;
 operating means acting on the pumping portion of the diaphragm and movable from an initial position to a diaphragm stressing position upon actuation of said operating means so as to move the diaphragm from its first position to its second position; the diaphragm returning to its first position, and causing return of the operating means to its initial position, by resilient relaxation of said diaphragm;
 the inlet valve comprising an apertured flexible resilient substantially liquid impermeable diaphragm is stretched, the curved surface being convexly curved in a direction away from the inlet conduit, the inlet conduit terminating at said curved surface at a location thereon remote from the position of registry of the aperture in the diaphragm with the curved surface.

9. The pump of claim 8 wherein the diaphragm of the inlet valve is integral with the diaphragm of the pumping member, and the outlet valve comprises an apertured flexible resilient substantially liquid impermeable diaphragm and a curved surface on the pump body over which the diaphragm is stretched, the curved surface of the outlet valve being convexly curved in a direction towards the outlet conduit, the outlet conduit terminating at said curved surface at a location thereon remote from the position of registry of the aperture in the diaphragm with the curved surface.

10. The pump of claim 9 further including an adjustable set screw engaging the operating means in its initial position, and adjustable to limit the stroke of the operating means on moving between its first and second positions, said set screw being accessible for adjustment externally of the body structure of the pump.

11. The pump of claim 9 wherein the diaphragm of the inlet valve, the diaphragm of the pumping chamber and the diaphragm of the outlet valve are all comprised of an integral, single diaphragm.

12. The pump of claim 11 wherein the body structure comprises a main body having said inlet conduit and said outlet conduit drilled therethrough, a valve plate secured to the bottom surface of the main body, the diaphragm being clamped between the main body and the valve plate, and a cover plate secured to the surface of the valve plate remote from the main body, the pump chamber and the communication between the pump chamber and the inlet valve and the outlet valve being formed by co-operating grooves in at least one of the adjacent surfaces of the valve plate and the cover plate.

* * * * *